United States Patent [19]

Maruo et al.

[11] Patent Number: 5,957,841
[45] Date of Patent: Sep. 28, 1999

[54] METHOD OF DETERMINING A GLUCOSE CONCENTRATION IN A TARGET BY USING NEAR-INFRARED SPECTROSCOPY

[75] Inventors: Katsuhiko Maruo, Itami; Masami Oka, Osaka, both of Japan

[73] Assignee: Matsushita Electric Works, Ltd., Kadoma, Japan

[21] Appl. No.: 09/046,580

[22] Filed: Mar. 24, 1998

[30] Foreign Application Priority Data

Mar. 25, 1997 [JP] Japan .......................................... 9-72150

[51] Int. Cl.⁶ .......................................................... A61B 5/00
[52] U.S. Cl. ............................. 600/316; 600/473; 356/39
[58] Field of Search ..................................... 600/316, 319, 600/322, 326, 473; 356/39; 439/63, 95

[56] References Cited

U.S. PATENT DOCUMENTS

| | | |
|---|---|---|
| 4,655,225 | 4/1987 | Dähne et al. . |
| 5,070,874 | 12/1991 | Barnes et al. . |
| 5,086,229 | 2/1992 | Rosenthal et al. . |
| 5,222,496 | 6/1993 | Clarke et al. . |
| 5,333,610 | 8/1994 | Hirao . |
| 5,379,764 | 1/1995 | Barnes et al. . |
| 5,434,412 | 7/1995 | Sodickson et al. . |
| 5,551,422 | 9/1996 | Simonsen et al. . |

FOREIGN PATENT DOCUMENTS

| | | |
|---|---|---|
| 0757243 A1 | 2/1997 | European Pat. Off. . |
| 2934190 A1 | 3/1981 | Germany . |

*Primary Examiner*—Eric F. Winakur
*Attorney, Agent, or Firm*—Armstrong, Westerman, Hattori, McLeland & Naughton

[57] ABSTRACT

A glucose concentration in a living tissue as a target is determined by the following method. Near-infrared radiation is projected on the living tissue, and a resulting radiation emitted from the living tissue is received. A spectrum analysis of the resulting radiation is performed to detect a first absorption signal from a wavelength region, e.g., 1550 nm to 1650 nm, having an absorption peak of OH group derived from glucose molecule, a second absorption signal from a wavelength region, e.g., 1480 nm to 1550 nm, having an absorption peak of NH group in the living tissue, and a third absorption signal from a wavelength region, e.g., 1650 nm to 1880 nm, having an absorption peak of CH group in the living tissue. The glucose concentration is determined by a multivariate analysis of results of the spectrum analysis, in which the first, second and third absorption signals are used as explanatory variables, and the glucose concentration is a criterion variable. This method can predict the glucose concentration of the subject with an improved accuracy.

12 Claims, 12 Drawing Sheets

METHOD OF DETERMINING A GLUCOSE CONCENTRATION IN A TARGET BY USING NEAR-INFRARED SPECTROSCOPY

BACKGROUND OF THE INVENTION

1. Field of the Invention

The present invention relates to a method of determining a glucose concentration in a target by using near-infrared spectroscopy, and particularly a method of non-invasive determination of a glucose concentration in the blood of a subject, which can be used to a health examination at home, or a blood sugar measurement for subjects such as a diabetic at medical facilities.

2. Disclosure of the Prior Art

Near-infrared spectroscopy has been widely used in various technical fields such as agriculture, food industry, or petrochemistry because it is a kind of non-destructive inspection, and does not need a peculiar operation for preparing a sample to be inspected. Since near-infrared radiation is a low energy electromagnetic wave, it is possible to avoid the occurrence of radiation damage of the sample. Near-infrared radiation is difficult to be absorbed by water as compared with intermediate-infrared radiation, therefore, it is possible to inspect a sample in an aqueous solution state. In addition, there is an advantage of a high transmittance of near-infrared radiation into a living body.

On the contrary, an intensity of absorption spectrum within a wavelength range of near-infrared radiation is very weak, e.g., about 1/100 of the intensity of absorption spectrum within a wavelength range of intermediate-infrared radiation. In addition, there is a problem that it is difficult to clarify the assignment of an absorption spectrum detected from the living body by the use of near-infrared radiation. These problems prevent an accurate quantum analysis of the glucose concentration by using the near-infrared spectroscopy.

U.S. Pat. No. 4,655,225 discloses a spectrophotometric method for non-invasive determination of glucose concentration in body tissues. A light provided from a directional optical light source is irradiated on a selected body portion, and then a resulting radiation emitted from the body portion is collected. The collected radiation includes at least one band with a wavelength of 1575 nm, 1756 nm, 2100 nm, and 2270±15 nm, typical of the glucose absorption spectrum, and at least one band with a reference wavelength in the range of 1000 nm to 2700 nm, typical of the absorption spectrum of background tissue. The absorption of glucose is nil or insignificant at the reference wavelength. After the collected radiation is converted into electrical signals, the glucose concentration of the subject is calculated by an electronic computer according to the electrical signals.

On the other hand, U.S. Pat. No. 5,070,874 discloses a method of non-invasive determination of the concentration of glucose in a patient. A near-infrared radiation over a limited range of wavelengths about 1660 nm is projected on a portion of the patient's body, and then the resulting radiation emitted from the portion is sensed. An expression for the magnitude of the resulting radiation as a function of wavelength is derived. The second derivative of the expression in a very narrow range at about 1660 nm, e.g., between 1640 nm and 1670 nm, is expanded. The glucose concentration of the patient is determined from the intensity of the resulting radiation at the maximum or minimum point of this derivative.

By the way, when determining the glucose concentration in a living tissue by using near-infrared spectroscopy, there is a tendency that absorption spectrums of water and components in the living tissue except for glucose overlap the absorption spectrums of glucose. FIGS. 12 and 13 show absorption spectrums of water, glucose (powder), albumin (powder), and cholesterol (powder), which are detected over wavelength ranges of first and second harmonic tones, respectively. For example, when an absorption spectrum of a target including water, glucose and albumin, is detected, it is expected that the absorption spectrums of water and albumin overlap a broad beak of the absorption spectrum of glucose at the vicinity of about 1580 nm, as understood from FIG. 12. In order to improve the accuracy of quantitative analysis of the glucose concentration, it is important to consider the influence of disturbance factors into the absorption spectrums of glucose.

Thus, there is room for further improvement in the methods of determining the glucose concentration of the prior art.

SUMMARY OF THE INVENTION

A primary object of the present invention is to provide a method of determining a glucose concentration in a target with an improved accuracy by using near-infrared spectroscopy. That is, near-infrared radiation is projected on the target, and a resulting radiation emitted from the target is received. A spectrum analysis of the resulting radiation is performed to detect at least one first absorption signal from a first wavelength region having an absorption peak of OH group derived from glucose molecule, at least one second absorption signal from a second wavelength region having an absorption peak of NH group in the target, and at least one third absorption signal from a third wavelength region having an absorption peak of CH group in the target. The glucose concentration is determined by a multivariate analysis of results of the spectrum analysis, in which the first, second and third absorption signals are used as explanatory variables, and the glucose concentration is a criterion variable.

When the spectrum analysis is performed over a first harmonic tone region, it is preferred that the first wavelength region is in a range of 1550 nm to 1650 nm, the second wavelength region is in a range of 1480 nm to 1550 nm, and the third wavelength region is in a range of 1650 nm to 1880 nm.

When the spectrum analysis is performed over a second harmonic tone region, it is preferred that the first wavelength region is in a range of 1050 nm to 1130 nm, the second wavelength region is in a range of 1000 nm to 1050 nm, and the third wavelength region is in a range of 1130 nm to 1300 nm.

It is also preferred that the first wavelength region is in a range of 1600±40 nm, the second wavelength region is in a range of 1530 ±20 nm, and the third wavelength region is in a range selected from the group of 1685±20 nm, 1715±20 nm, and 1740±20 nm.

In a preferred embodiment of the present invention, the first absorption signal is an absorbency at a first wavelength in the first wavelength region, the second absorption signal is an absorbency at a second wavelength in the second wavelength region, and the third absorption signal is an absorbency at a third wavelength in the third wavelength region. The first, second and third wavelengths can be determined by the following procedure. A plurality of test samples having different concentrations in a system including albumin, glucose, and water, are prepared, and absorption spectrums of the test samples are measured.

Alternatively, a glucose tolerance test is applied to a subject, and absorption spectrums of the subject during the glucose tolerance test are measured. A multivariate analysis of the measured absorption spectrums is performed to obtain a profile indicative of a relation between wavelength and regression coefficient. From this profile, a wavelength substantially corresponding to a peak of the regression coefficient within the first wavelength region is selected as the first wavelength. A wavelength substantially corresponding to a peak of the regression coefficient within the second wavelength region is selected as the second wavelength. A wavelength substantially corresponding to a peak of the regression coefficient within the third wavelength region is selected as the third wavelength.

In a further preferred embodiment of the present invention, the near-infrared radiation projected on the target essentially consists of a first near-infrared radiation having a center wavelength and a half-width within the first wavelength region, a second near-infrared radiation having a center wavelength and a half-width within the second wavelength region, and a third near-infrared radiation having a center wavelength and a half-width within the third wavelength region. For example, the center wavelength and the half-width of the first near-infrared radiation can be determined by the following procedure. A plurality of test samples having different concentrations in a system including albumin, glucose, and water, are prepared, and absorption spectrums of the test samples are measured. Alternatively, a glucose tolerance test is applied to a subject, and absorption spectrums of the subject during the glucose tolerance test are measured. A multivariate analysis of the measured absorption spectrums is performed to obtain a profile indicative of a relation between wavelength and regression coefficient. From this profile, a wavelength substantially corresponding to a maximum value of the regression coefficient within the first wavelength region is selected as the center wavelength of the first near-infrared radiation, and a wavelength region substantially corresponding to 70% or more of the maximum value within the first wavelength region is selected as the half-width of the first near-infrared radiation. In particular, it is preferred that the center wavelength of the first near-infrared radiation is determined within a range of 1560 nm to 1640 nm, and the half-width thereof is 60 nm or less.

These and still other objects and advantages will become apparent from the following description of the preferred embodiments of the invention when taken in conjunction with the attached drawings.

DETAIL DESCRIPTION OF THE PREFERRED EMBODIMENTS

First Embodiment

The first embodiment of the present invention provides a method of determining a glucose concentration in a bovine serum sample by using near-infrared spectroscopy.

First, a plurality of bovine serum samples having different concentrations of glucose and albumin are prepared. Albumin is a quite ordinary protein component in the blood, and will work as a disturbance factor in a spectrum analysis for determining the glucose concentration. This is the reason why albumin is included in the bovine serum samples. 5 ml of a glucose aqueous solution and 15 ml of an albumin aqueous solution are mixed with 80 ml of a bovine serum to obtain each of the bovine serum samples. The glucose concentrations in the bovine serum samples are 30 mg/dl, 93 mg/dl, 155 mg/dl, 280 mg/dl, 530 mg/dl, and 1030 mg/dl. The albumin concentrations in the bovine serum samples are 2.24 g/dl, 2.84 g/dl, 3.44 g/dl, 4.64 g/dl, and 5.84 g/dl. Therefore, it is possible to prepare the bovine serum samples having 30 (5×6) different concentrations of glucose and albumin. In this embodiment, 15 bovine serum samples optionally selected from the 30 different bovine serum samples are used. Thus, since the concentrations of glucose, albumin and water, are changed in these bovine serum samples, it is difficult to accurately determine the glucose concentration by simply considering a relation between water and glucose. The influence of albumin of the disturbance factor must be also considered to accurately determine the glucose concentration.

Figure 1:
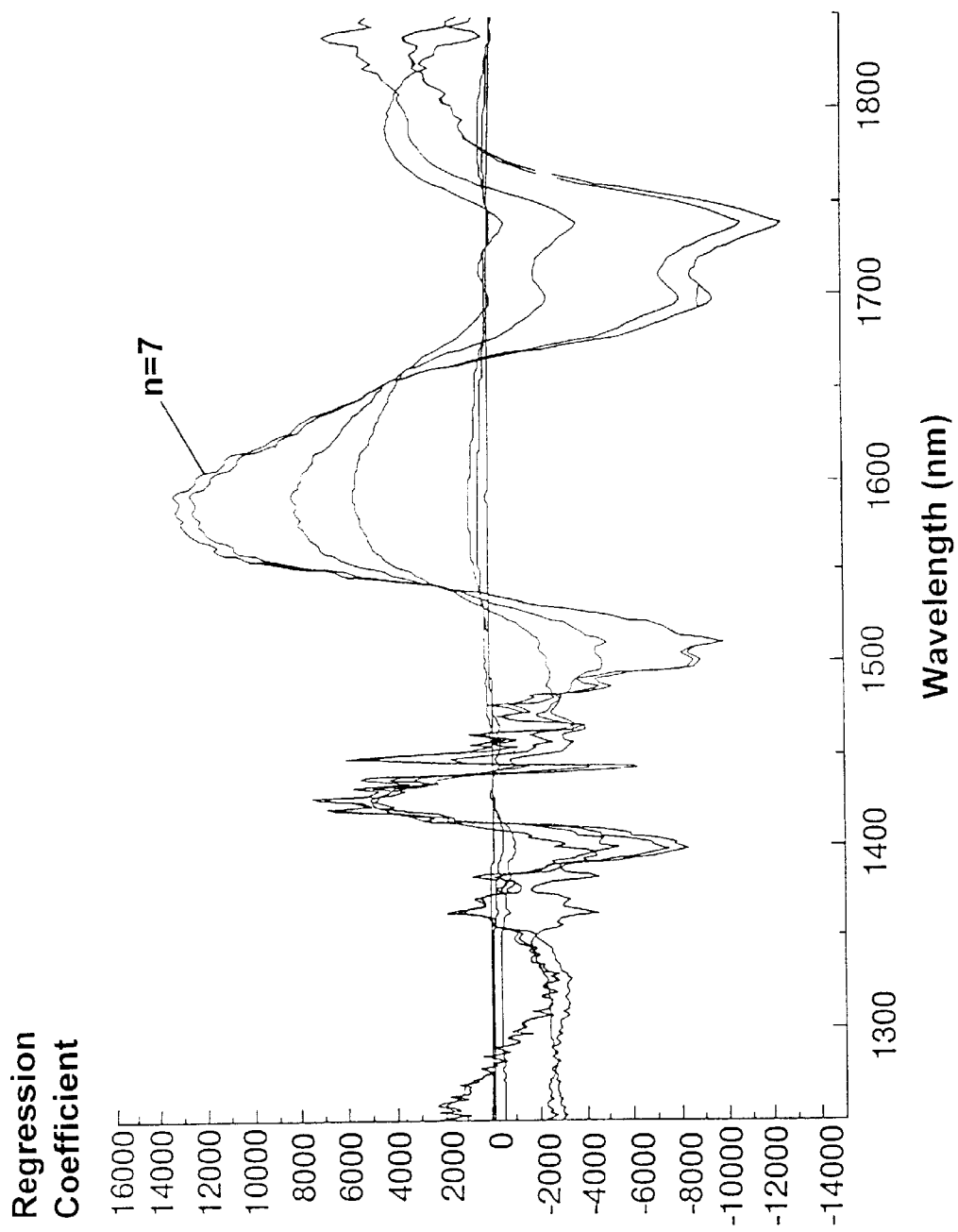
FIG. 1 is profiles showing relations between wavelength and regression coefficient of a first embodiment of the present invention.

A spectrum measurement of each of the bovine serum samples is performed by using MAGNA 850 (manufactured by "NICOLET") under conditions of arithmetic mean 128, resolution 16, a detector DTGS KBr, and a white light source. After the measured absorption signals are converted to absorbencies by using a reference signal stored in a memory in an FT-IR to obtain spectrum data, PLS (Partial Least Squares) regression analysis of the spectrum data is performed over 1250 nm to 1850 nm, in which harmonics of a first harmonic tone are observed, by using a marketed software of multivariate analysis. In this PLS regression analysis, the glucose concentration is a criterion variable, and the absorbencies are explanatory variables. FIG. 1 is profiles showing relations between wavelength and regression coefficient, which are obtained by analyzing with respect to a plurality of principal components. Results of the PLS regression analysis by the use of a seventh principal component (n=7) show that a correlation coefficient at the preparation of a calibration line is 0.996, a standard error (SEP) is 28.1 mg/dl, a correlation coefficient at the validation of the calibration line is 0.992, and a standard error (SEP) is 38.1 mg/dl. In place of the PLS regression analysis, it is possible to use principal component analysis.

Next, a multiple regression equation as a calibration line of the is glucose concentration is determined by the procedure explained below. The multiple regression equation is expressed by the following equation:

$$Y = a1x1 + a2x2 + a3x3 + a0$$

wherein x1, x2 and x3 are explanatory variables, Y is a criterion variable, a1, a2, and a3 are regression coefficients, and a0 is a constant. The criterion variable is the glucose concentration. The explanatory variables x1 to x3 are determined from the profile of FIG. 1. That is, an absorbency at about 1590 nm is used as the explanatory variable (x1). The wavelength of 1590 nm substantially corresponds to a wavelength of a positive peak observed in a first wavelength region (1550~1650 nm) having an absorption peak derived from OH group of glucose molecule, as shown in the profile (n=7) of FIG. 1. An absorbency at about 1525 nm is used as the explanatory variable (x2). The wavelength of 1525 nm corresponds to a wavelength at the vicinity of a negative peak observed in a second wavelength region (1480~1550 nm) having an absorption peak derived from NH group in the bovine serum sample. An absorbency at about 1690 nm is used as the explanatory variable (x3). The wavelength of 1690 nm corresponds to a wavelength at the vicinity of a negative peak observed in a third wavelength region (1650~1850 nm) having an absorption peak derived from CH group in the bovine serum sample.

A multivariate analysis is performed by using the criterion variable and these explanatory variables to determine the regression coefficients (a1–a3) and the constant a0 and complete the calibration line. Results of the multivariate analysis show that a correlation coefficient at the preparation of the calibration line is 0.983, a standard error (SEP) is 57.0 mg/dl, a correlation coefficient at the validation of the calibration line is 0.981, and a standard error (SEP) is 60.1 mg/dl.

Second Embodiment

The second embodiment of the present invention provides a method of determining a glucose concentration in a bovine serum sample by using near-infrared spectroscopy.

First, a plurality of bovine serum samples having different concentrations of glucose and albumin are prepared. 5 ml of a glucose aqueous solution and 15 ml of an albumin aqueous solution are mixed with 80 ml of a bovine serum to obtain each of the bovine serum samples. The glucose concentrations in the bovine serum samples are 35 mg/dl, 136 mg/dl, 220 mg/dl, 412 mg/dl, and 750 mg/dl. The albumin concentrations in the bovine serum samples are 2.6 g/dl, 3.0 g/dl, 3.3 g/dl, 4.0 g/dl, and 5.4 g/dl. Therefore, it is possible to prepare the bovine serum samples having 25 (5×5) different concentrations of glucose and albumin. In this embodiment, 13 bovine serum samples optionally selected from the 25 different bovine serum samples are used.

Figure 2:
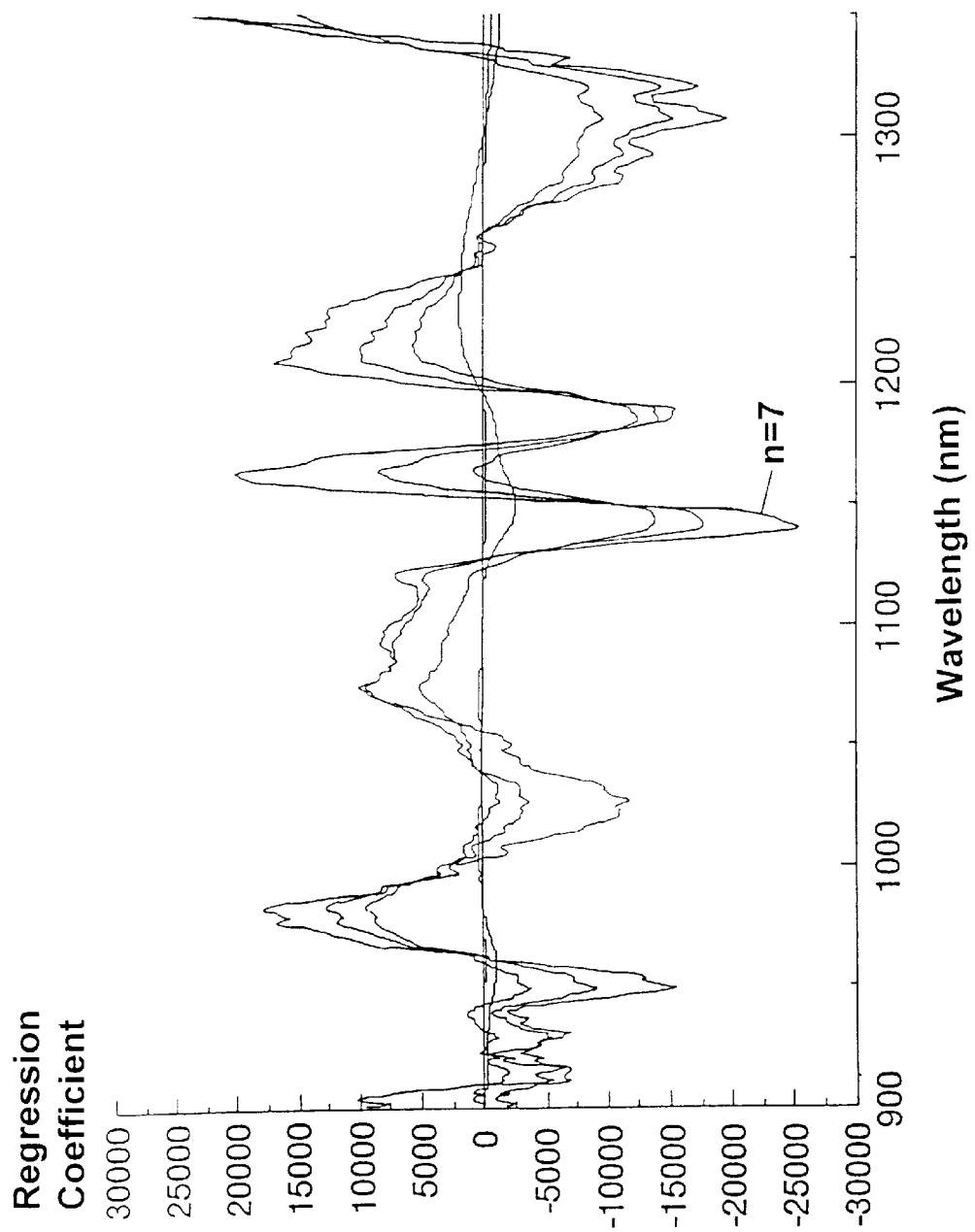
FIG. 2 is profiles showing relations between wavelength and regression coefficient of a second embodiment of the present invention.

A spectrum measurement of each of the bovine serum samples is performed by the same procedure as the first embodiment except for the detector is cooled by liquid nitrogen. After the measured absorption io signals are converted to absorbencies by using a reference signal stored in a memory in an FT-IR to obtain spectrum data, PLS regression analysis of the spectrum data is performed over 900 nm to 1350 nm, in which harmonics of a second harmonic tone are observed, by using a marketed software of multivariate analysis. The PLS regression analysis is performed to absorption spectrums smoothed by a moving average method by 17 points. In this PLS regression analysis, the glucose concentration is a criterion variable, and the absorbencies are explanatory variables. FIG. 2 is profiles showing relations between wavelength and regression coefficient, which are obtained by analyzing with respect to a plurality of principal components. Results of the PLS regression analysis by the use of a seventh principal component (n=7) show that a correlation coefficient at the preparation of a calibration line is 0.981, a standard error (SEP) is 53.1 mg/dl, a correlation coefficient at the validation of the calibration line is 0.959, and a standard error (SEP) is 77.2 mg/dl.

In this embodiment, the determination of the glucose concentration is performed by using an absorbency at the vicinity of 1020 nm having a negative peak derived from NH group of albumin molecule, absorbency at the vicinity of 1070 nm having a positive peak derived from OH group of glucose molecule, and an absorbency at the vicinity of 1150 nm having a negative peak derived from CH group of albumin molecule, as shown in FIG. 2.

Third Embodiment

The third embodiment of the present invention provides a method of determining a glucose concentration in a bovine serum sample by using near-infrared spectroscopy.

First, a plurality of bovine serum samples having different concentrations of glucose, albumin, cholesterol, neutral fat, and water, are prepared. The glucose concentrations in the bovine serum samples are 35 mg/dl, 85 mg/dl, 140 mg/dl, 220 mg/dl, 270 mg/dl, 415 mg/dl, 510 mg/dl, 800 mg/dl, 985 mg/dl, 1500 mg/dl. The albumin concentrations in the bovine serum samples are 2.2 g/dl, 2.3 g/dl, 2.4 g/dl, 2.5 g/dl, 2.8 g/dl, 3.4 g/dl, 4.5 g/dl, and 5.4 g/dl. The cholesterol concentrations in the bovine serum samples are 55 mg/dl, 63 mg/dl, 70 mg/dl, 75 mg/dl, 83 mg/dl, 100 mg/dl, 135 mg/dl, 205 mg/dl, and 350 mg/dl. The neutral fat concentrations in the bovine serum samples are 10 mg/dl, 15 mg/dl, 20 mg/dl, 70 mg/dl, 133 mg/dl, 250 mg/dl, and 480 mg/dl. In this embodiment, 45 bovine serum samples optionally selected from a large number of combinations of these concentrations are used.

Figure 3:
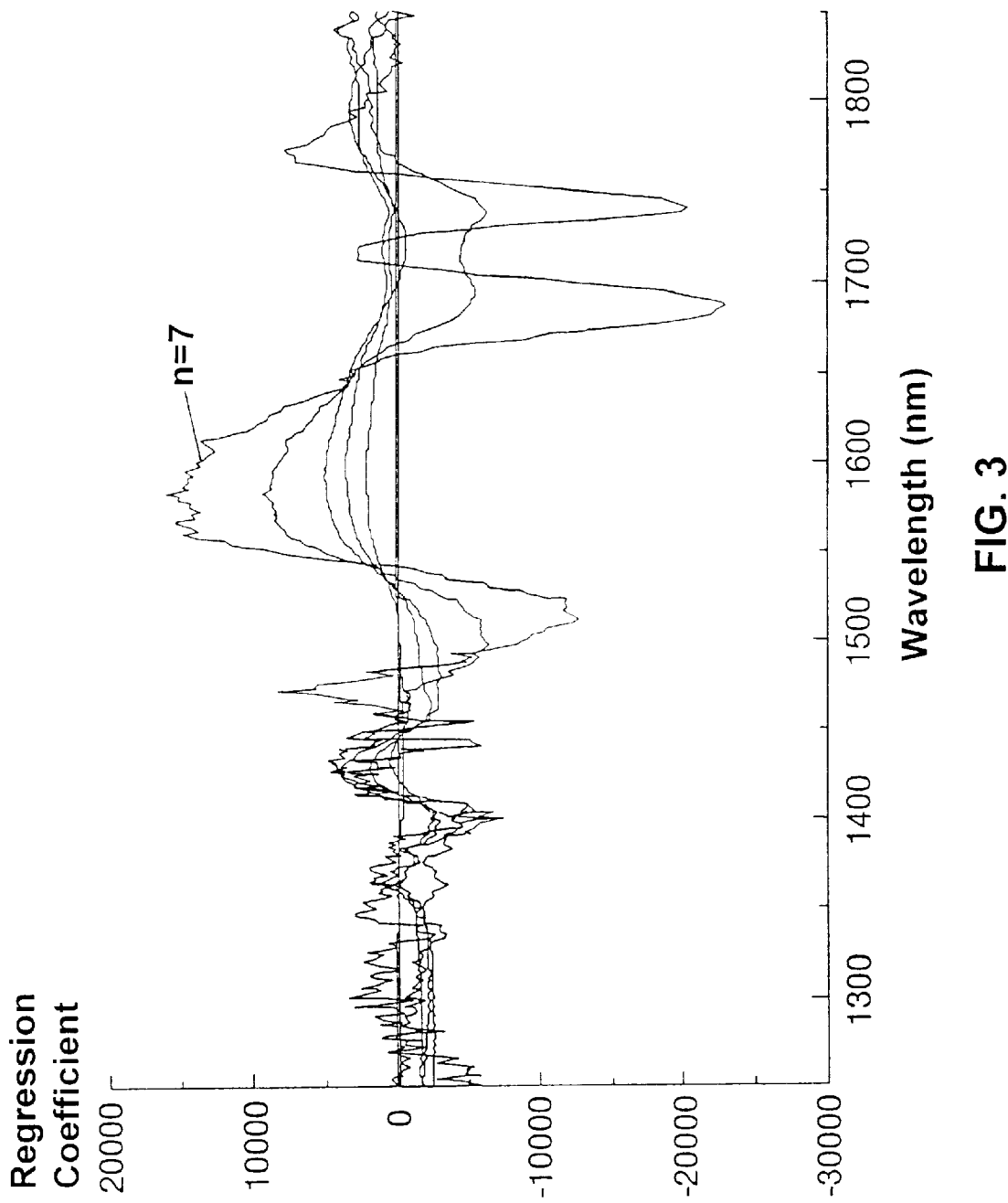
FIG. 3 is profiles showing relations between wavelength and regression coefficient of a third embodiment of the present invention

A spectrum measurement of each of the bovine serum samples is performed by the same procedure as the first embodiment. After the measured absorption signals are converted to absorbencies to obtain spectrum data, PLS regression analysis of the spectrum data is performed over a wavelength range of 1480 nm to 1850 nm, in which harmonics of a first harmonic tone are observed, by using a marketed software of multivariate analysis. In this PLS regression analysis, the glucose concentration is a criterion variable, and the absorbencies are used as explanatory variables. FIG. 3 is profiles showing relations between wavelength and regression coefficient, which are obtained by analyzing with respect to a plurality of principal components. Results of the PLS regression analysis by the use of a seventh principal component (n=7) show that a correlation coefficient at the preparation of a calibration line is 0.992, a standard error (SEP) is 48.7 mg/dl, a correlation coefficient at the validation of the calibration line is 0.991, and a standard error (SEP) is 51.1 mg/dl. In place of the PLS regression analysis, it is possible to use principal component analysis.

Next, a multiple regression equation as a calibration line of the glucose concentration is determined by the procedure explained below. The multiple regression equation is expressed by the following equation:

$$Y=a1x1+a2x2+a3x3+a4x4+a5x5+a6x6+a7x7+a0$$

wherein x1, x2, x3, x4, x5, x6, and x7 are explanatory variables, Y is a criterion variable, a1, a2, a3, a4, a5, a6 and a7 are regression coefficients, and a0 is a constant. The criterion variable is the glucose concentration. The explanatory variables x1 to x7 are determined from the profiles of FIG. 3. That is, an absorbency at 1580 nm is used as the explanatory variable (x1). The wavelength of 1580 nm substantially corresponds to a wavelength of a positive peak observed in a first wavelength region (1550–1650 nm) having an absorption peak derived from OH group of glucose molecule, as shown in the profile (n=7) of FIG. 3. An absorbency at about 1520 nm is used as the explanatory variable (x2). The wavelength of 1520 nm substantially corresponds to a wavelength of a negative peak observed in a second wavelength region (1480–1550 nm) having an absorption peak derived from NH group in the bovine serum sample. Absorbencies at about 1685 nm, 1715 nm, and 1740 nm, are used as the explanatory variables (x3, x4, x5), respectively. These wavelengths substantially correspond to negative and positive peaks observed in a third wavelength region (1650–1880 nm) having absorption peaks derived from CH group in the bovine serum sample. An absorbency at about 1540 nm is used as the explanatory variable (x6). The wavelength of 1540 nm substantially corresponds to a wavelength of an intersection of the profiles of FIG. 3 at the vicinity of a boundary between the first and second wavelength regions. An absorbency at about 1645 nm is used as the explanatory variable (x7). The wavelength of 1645 nm substantially corresponds to a wavelength of an intersection of the profiles of FIG. 3 at the vicinity of a boundary between the second and third wavelength regions.

A multivariate analysis is performed by using the criterion variable and these explanatory variables to determine the regression coefficients (a1–a7) and the constant a0, and complete the calibration line. Results of the multivariate analysis show that a correlation coefficient at the preparation of the calibration line is 0.989, a standard error (SEP) is 55.6 mg/dl, a correlation coefficient at the validation of the calibration line is 0.988, and a standard error (SEP) is 57.8 mg/dl.

Prior to the multivariate analysis, it is preferred to perform a pretreatment of subtracting the value of wavelength substantially corresponding to an intersection of the profiles of FIG. 3 from the absorbencies. Alternatively, it is preferred to perform a pretreatment of dividing the absorbencies by the wavelength value at the vicinity of the intersection.

Fourth Embodiment

Figure 4:
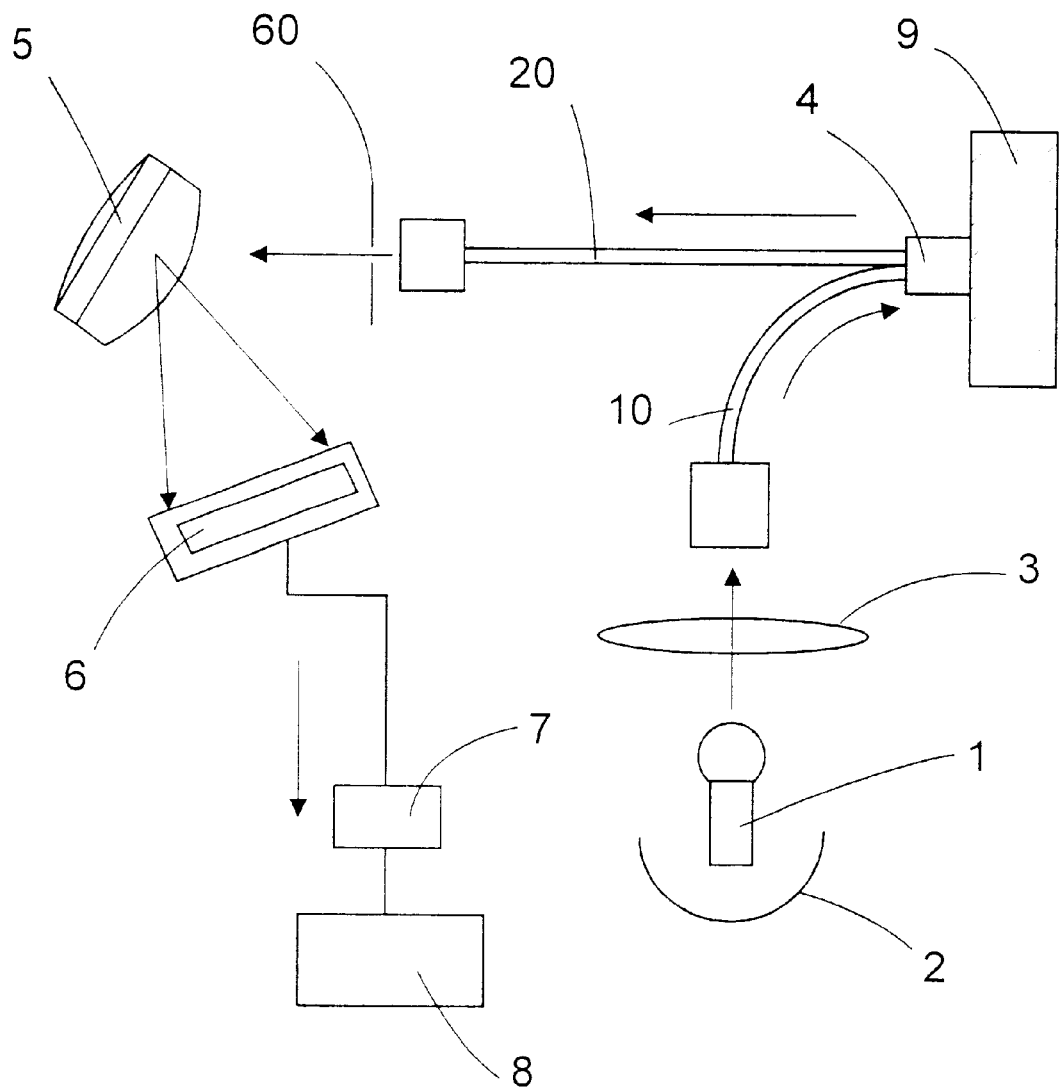
FIG. 4 is a schematic diagram of a device for non-invasive determination of a glucose concentration in the blood of a subject used in a fourth embodiment of the present invention.

A schematic diagram of a device of non-invasive determination of a glucose concentration in the blood of a subject is shown in FIG. 4. The device comprises a halogen lamp 1 an a light source, first optical fibers 10 for introducing near-infrared radiation provided from the halogen lamp to a body portion 9 of the subject, second optical fibers 20 for receiving a resulting radiation emitted from the body portion, an optical fiber bundle 4 formed with the first and second optical fibers, a flat-field type diffraction grating unit 5 as a spectroscope of the resulting radiation, an array-type photo diode 6 as a detector of the absorption signals, and an operation unit 8 comprising a microcomputer for determining the glucose concentration of the subject according to outputs of the array-type photo diode. In the operating unit 8, after the absorption signals are converted to absorbencies, the glucose concentration of the subject is calculated by the use of a predetermined calibration line. In FIG. 4, numeral 2 designates a reflection mirror. Numeral 3 designates a lens system disposed between the halogen lamp 1 and the first optical fibers 10. Numeral 60 designates a slit disposed between the diffraction grating unit 5 and the second optical fibers 20. Numeral 7 designates an A/D converter.

Figure 5:
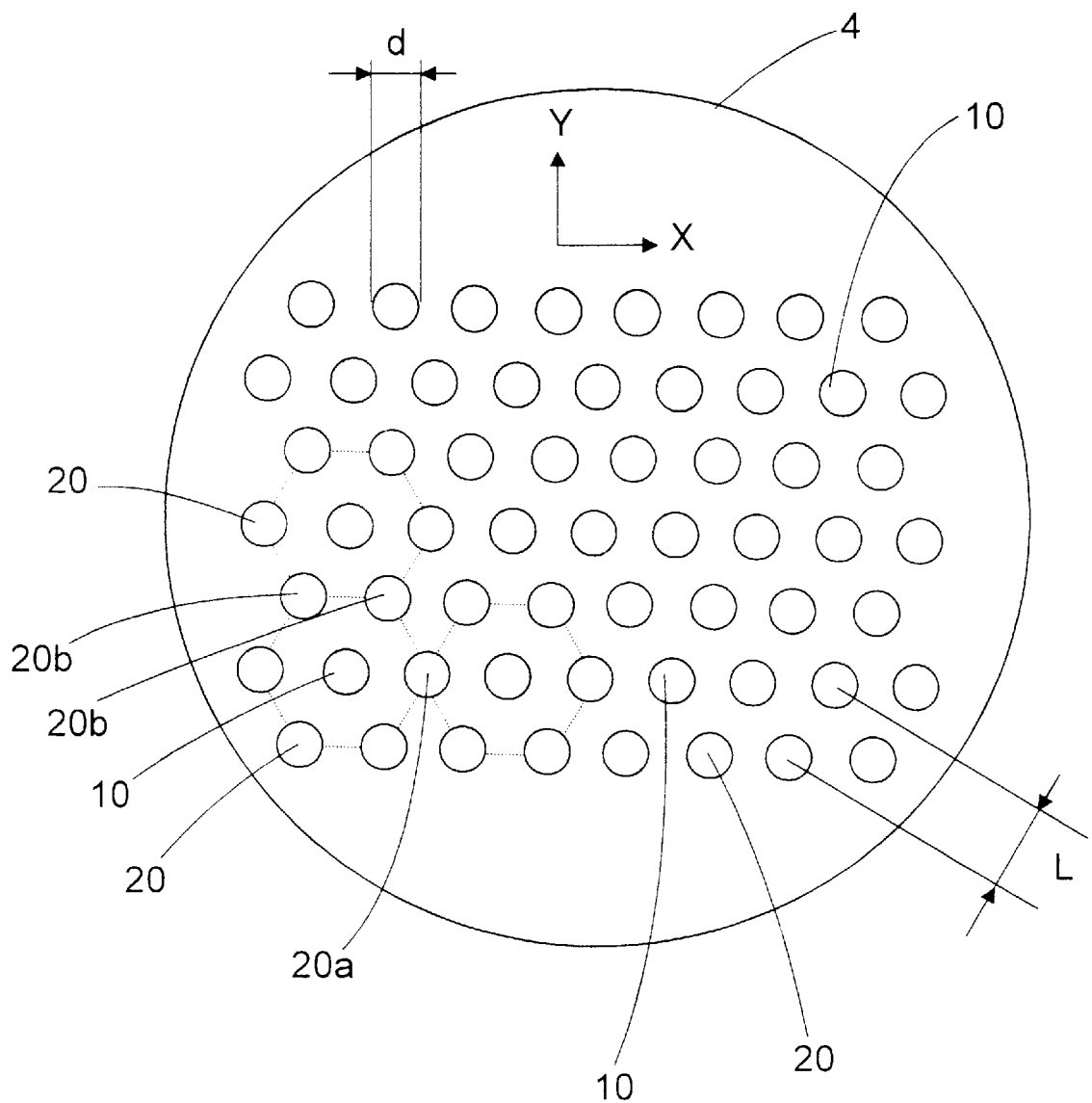
FIG. 5 is an end view of an optical fiber bundle used in the fourth embodiment.

The optical fiber bundle 4 is formed with a plurality of sub-bundles, in each of which a projection end of the first optical fiber 10 is disposed on an end surface of the bundle at a center of a hexagonal pattern, as shown by a dotted line in FIG. 5, and six receiving ends of the second optical fibers 20 are disposed at corners of the hexagonal pattern. A receiving end 20a of each of the sub-bundles is common with an adjacent sub-bundle in an X-axis direction. Two receiving ends 20b of each of the sub-bundles are common with an adjacent sub-bundle in a Y-axis direction.

In each of the sub-bundles, a distance L between centers of the projection end of the first optical fiber 10 and an adjacent receiving end of the second optical fiber 20 is 0.5 mm. It is preferred to determine the distance L within a range of 0.1 mm to 2 mm, and more preferably a range of 0.2 mm to 1 mm. This optical fiber bundle 4 is designed to selectively extract spectrum information from a dermis layer of the skin of the subject. In this embodiment, a diameter of each of the first and second optical fibers (10, 20) is 200 $\mu$m. The end surface of the bundle 4 is pressed normally against a skin surface of the forearm of the subject. It is preferred to use a pressure gauge and a fixture for pressing the bundle 4 against the skin surface by a required pressure.

The fourth embodiment of the present invention provides a method of determining the glucose concentration in the blood of a subject by using the device of FIG. 4.

Figure 6:
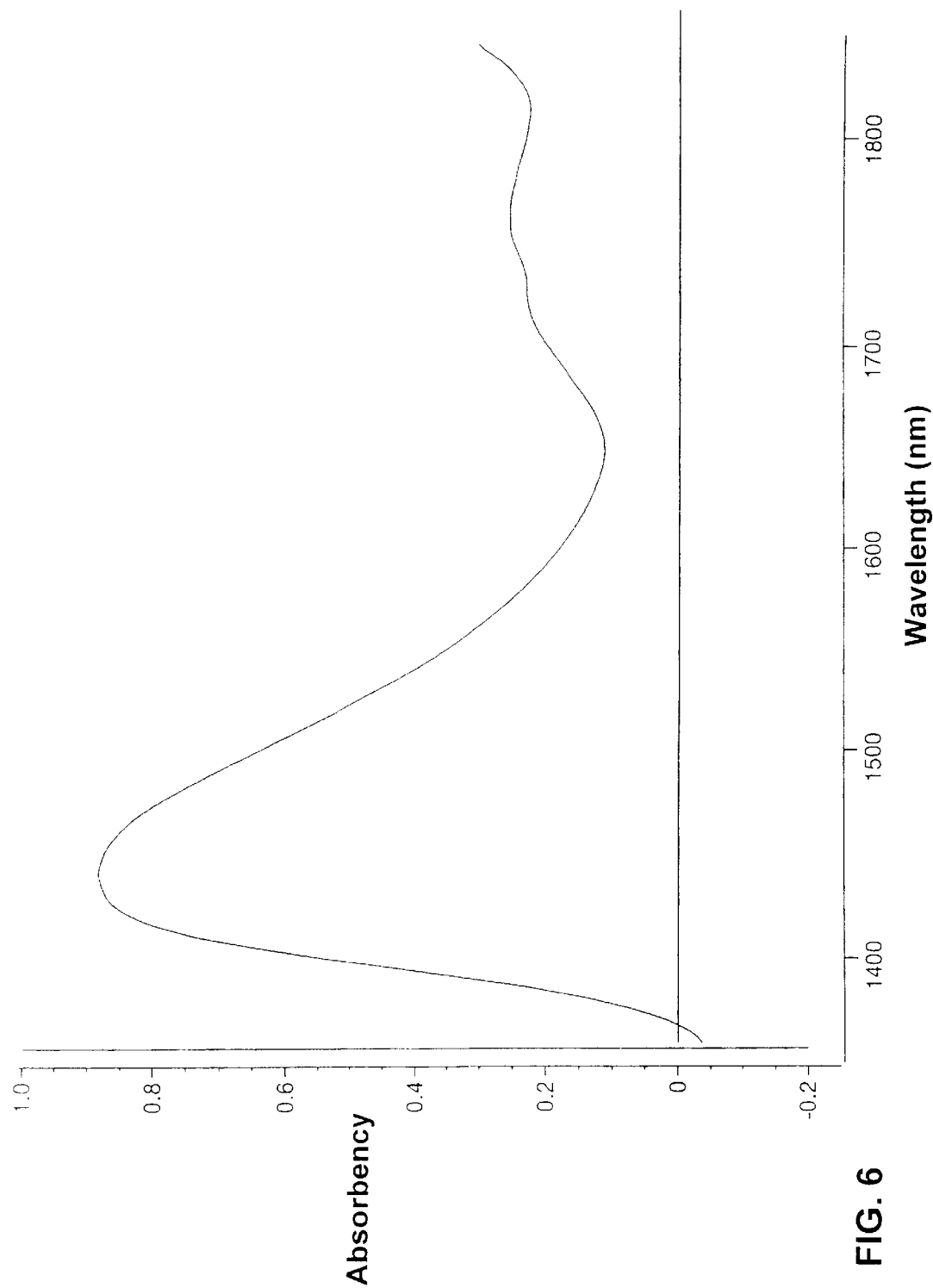
FIG. 6 is an absorption spectrum detected in the fourth embodiment.

An experiment is performed to a subject of a healthy male, thirty years of age, according to the procedure explained below. The subject is kept at a rest state for 30 minutes, and then a medicine of partial hydrolysate of starch is ingested by the subject. An amount of the medicine corresponds to about 75 g of glucose. An invasive measurement of the glucose concentration in the blood of the subject is performed every 10 minutes for 90 minutes from the start of keeping the subject at the rest state by using a simplified blood sugar measuring device of a blood-taking type. The blood of the subject is taken from the tip of a finger. A non-invasive measurement of absorption spectrums of the subject is repeated four times by using the device of FIG. 4 at the lapse of 5 minutes from each of the invasive measurements of the glucose concentration. A profile of the measured absorption spectrum of the subject is shown in FIG. 6. In this embodiment, the time lag of 5 minutes between the invasive and noninvasive measurements is adopted to consider a time difference necessary for the correspondence between the glucose concentrations in the blood of the tip of finger and in the vicinity of the skin surface of the forearm. The glucose concentration in the blood of the subject is changed within a range of 89 to 134 mg/dl during the invasive measurements.

Figure 7:
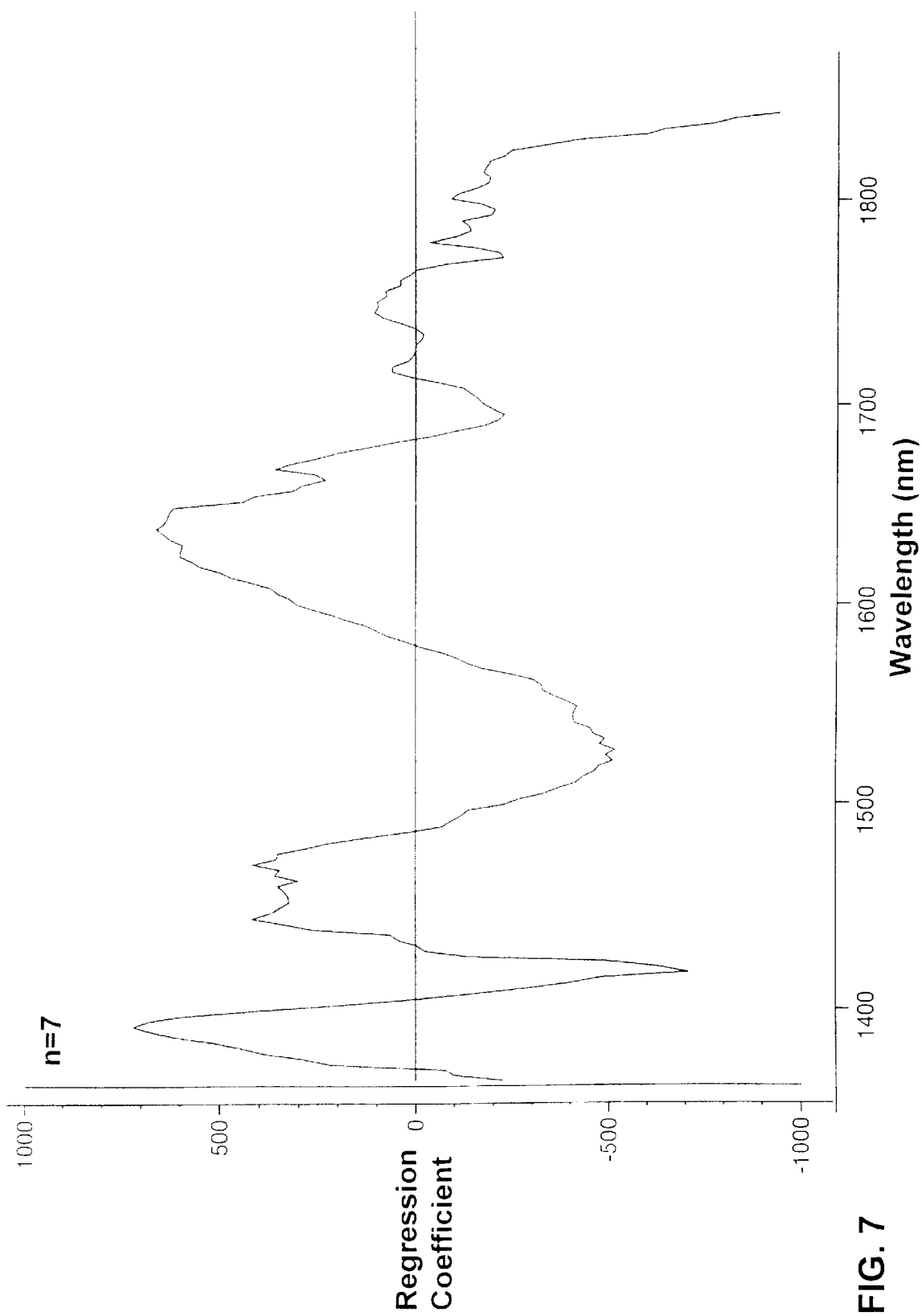
FIG. 7 is a profile showing a relation between wavelength and egression coefficient of the fourth embodiment.

Next, PLS regression analysis is performed over a wavelength region of 1350 nm to 1850 nm, in which harmonics of a first harmonic tone are observed, by using a cross validation method. In this PLS regression analysis, the glucose concentration is a criterion variable, and the absorbencies are used as explanatory variables. FIG. 7 is a profile showing a relation between wavelength and regression coefficient, which is obtained by analyzing with respect to a seven principal component (n=7). Results of the PLS regression analysis show that a correlation coefficient at the preparation of a calibration line is 0.993, a standard error (SEP) is 1.9 mg/dl, a correlation coefficient at the validation of the calibration line is 0.988, and a standard error (SEP) is 2.6 mg/dl.

A multiple regression equation as a calibration line of the glucose concentration in the blood is determined by the procedure explained below. The multiple regression equation is expressed by the following equation:

$$Y = a1x1 + a2x2 + a3x3 + a0$$

wherein x1, x2 and x3 are explanatory variables, Y is a criterion variable, a1, a2, and a3 are regression coefficients, and a0 is a constant. The criterion variable is the glucose concentration. The explanatory variables x1 to x3 are determined from the profile of FIG. 7. That is, an absorbency at about 1640 nm is used as the explanatory variable (x1). The wavelength of 1640 nm substantially corresponds to a wavelength of a positive peak observed in a first wavelength region (1600±40 nm) having an absorption peak derived from OH group of glucose molecule, as shown in the profile of FIG. 7. An absorbency at about 1550 nm is used as the explanatory variable (x2). The wavelength of 1550 nm substantially corresponds to a wavelength of a negative peak observed in a second wavelength region (1530±20 nm) having an absorption peak derived from NH group in the living tissue of the subject. An absorbency at about 1690 nm is used as the explanatory variable (x3). The wavelength of 1690 nm substantially corresponds to a wavelength of a negative peak observed in a third wavelength region (1685±20 nm) having an absorption peak derived from CH group in the living tissue. If necessary, it is preferred to use a body temperature of the subject as an additional explanatory variable.

Figure 8:
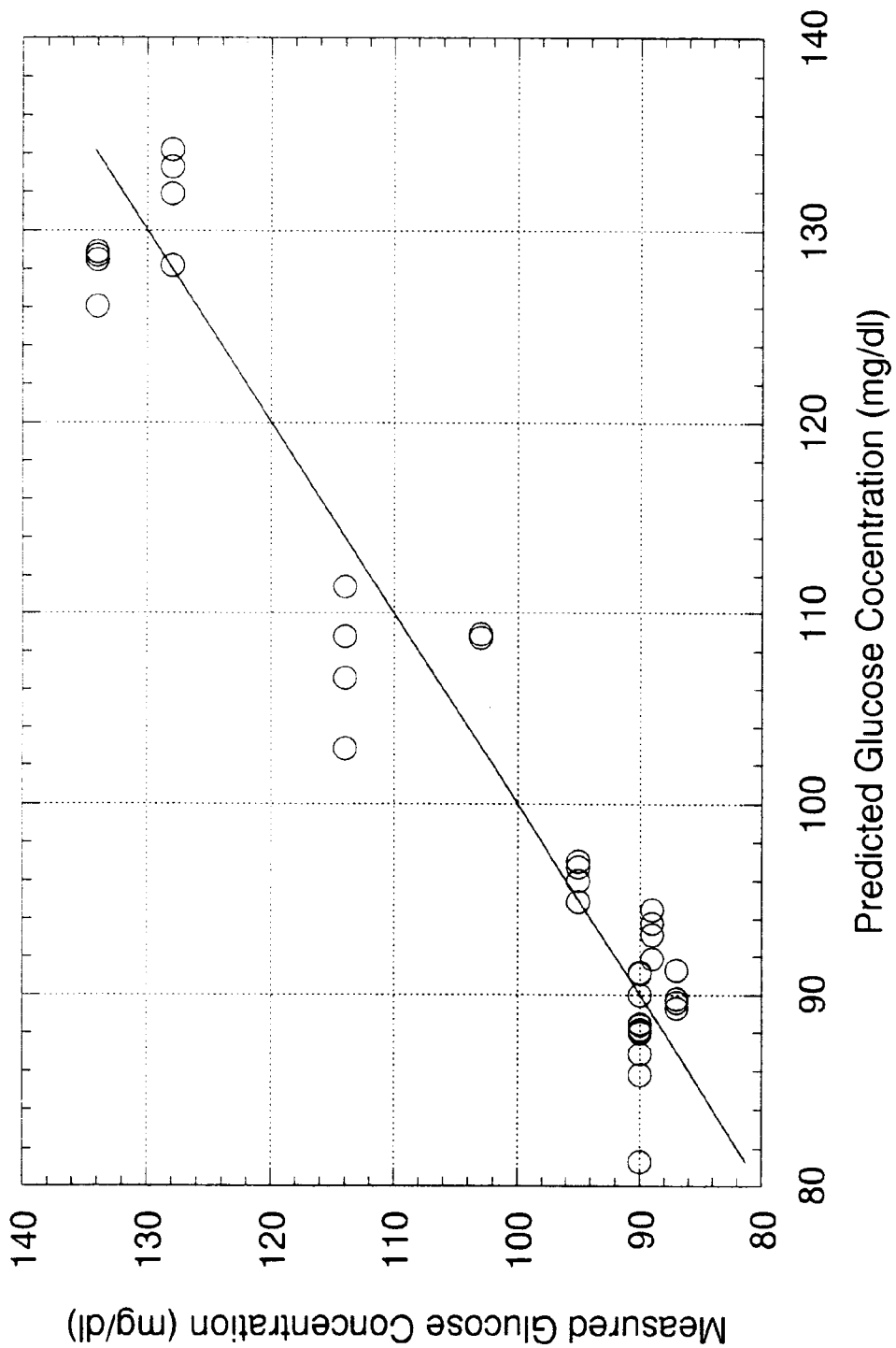
FIG. 8 is a calibration line of the glucose concentration obtained in the fourth embodiment.

A multivariate analysis is performed by using the criterion variable and these explanatory variables to determine the regression coefficients (a1–a3) and the constant a0 and complete the calibration line. Results of the multivariate analysis show that a correlation coefficient at the preparation of the calibration line is 0.957, a standard error (SEP) is 4.8 mg/dl, a correlation coefficient at the validation of the calibration line is 0.949, and a standard error (SEP) is 5.3 mg/dl. FIG. 8 shows the calibration line obtained by the multivariate analysis. In FIG. 8, glucose concentration values predicted from the measured absorption spectrums are also plotted.

Fifth Embodiment

Figure 9:
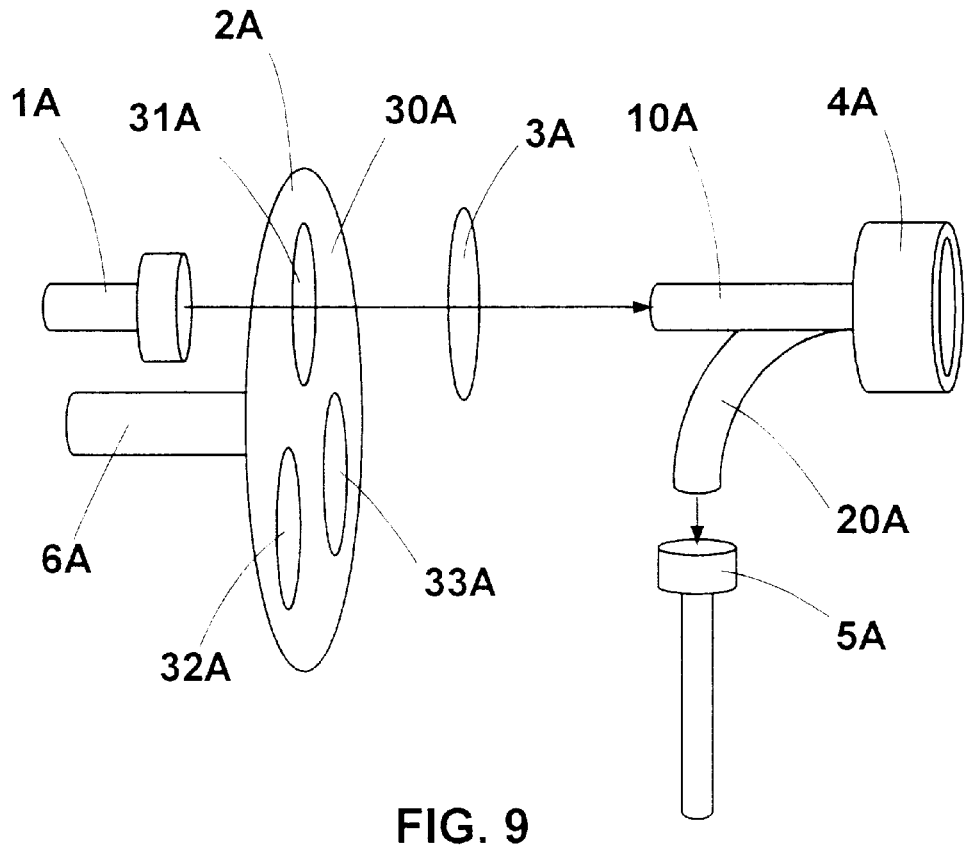
FIG. 9 is a schematic diagram of a device for non-invasive determination of a glucose concentration in the blood of a subject used in a fifth embodiment of the present invention.
Figure 10:
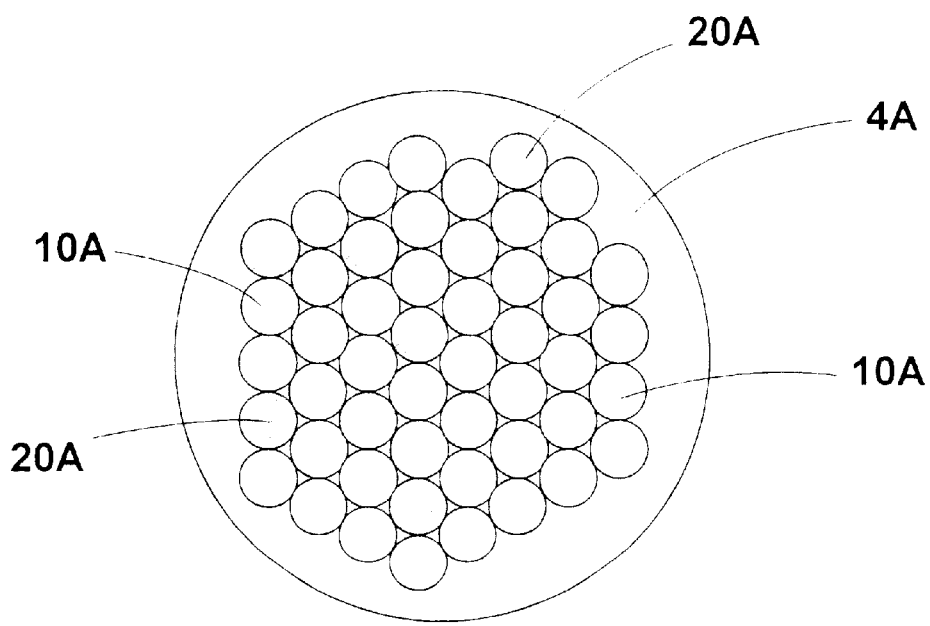
FIG. 10 is an end view of an optical fiber bundle used in the fifth embodiment.

A schematic diagram of a device of non-invasive determination of a glucose concentration in the blood of a subject is shown in FIG. 9. The device comprises a light-emitting diode 1A as a near-infrared radiation source, a spectroscope 2A of the near-infrared radiation, a lens 3A for collecting the near-infrared radiation, first optical fibers 10A for introducing the collected light to a body portion of the subject, second optical fibers 20A for receiving a resulting radiation emitted from the body portion, an optical fiber bundle 4A formed with the first and second optical fibers, a photo diode 5A as a detector of the resulting radiation, and an operation unit (not shown) for calculating the glucose concentration from outputs of the photo diode. A pattern of projection ends of the first optical fibers 10A and receiving ends of the second optical fibers 20A arranged on an end surface of the fiber bundle 4A is shown in FIG. 10. Each of the first and second optical fibers (10A, 20A) has a diameter of 500 μm. A distance between centers of the projection end of the first optical fiber 10A and an adjacent receiving end of the second optical fiber 20A is 500 μm.

As the light-emitting diode 1A, there are light-emitting diodes of InP system useable in first and second harmonic tone regions, and light-emitting diodes of GaAs system, or GaAlAs system useable in a third harmonic tone region. In this embodiment, a light-emitting diode of InP system having a center wavelength 1600 nm and a half-width of 160 nm is used. The spectroscope 2A is formed with a disc 30A, and a set of first, second and third interference filters (31A, 32A, 33A) disposed around a center of the disc. The disc 30A can be rotated by a motor 6A to select a required one from the first to third interference is filters. The first interference filter 31A is used to provide a first near-infrared radiation having a center wavelength of 1585 nm and a half-width of 60 nm. The second interference filter 32A is used to provide a second near-infrared radiation having a center wavelength of 1530 nm and a half-width of 10 nm. The third interference filter 33A is used to provide a third near-infrared radiation having a center wavelength of 1680 nm and a half-width of 10 nm.

Figure 11:
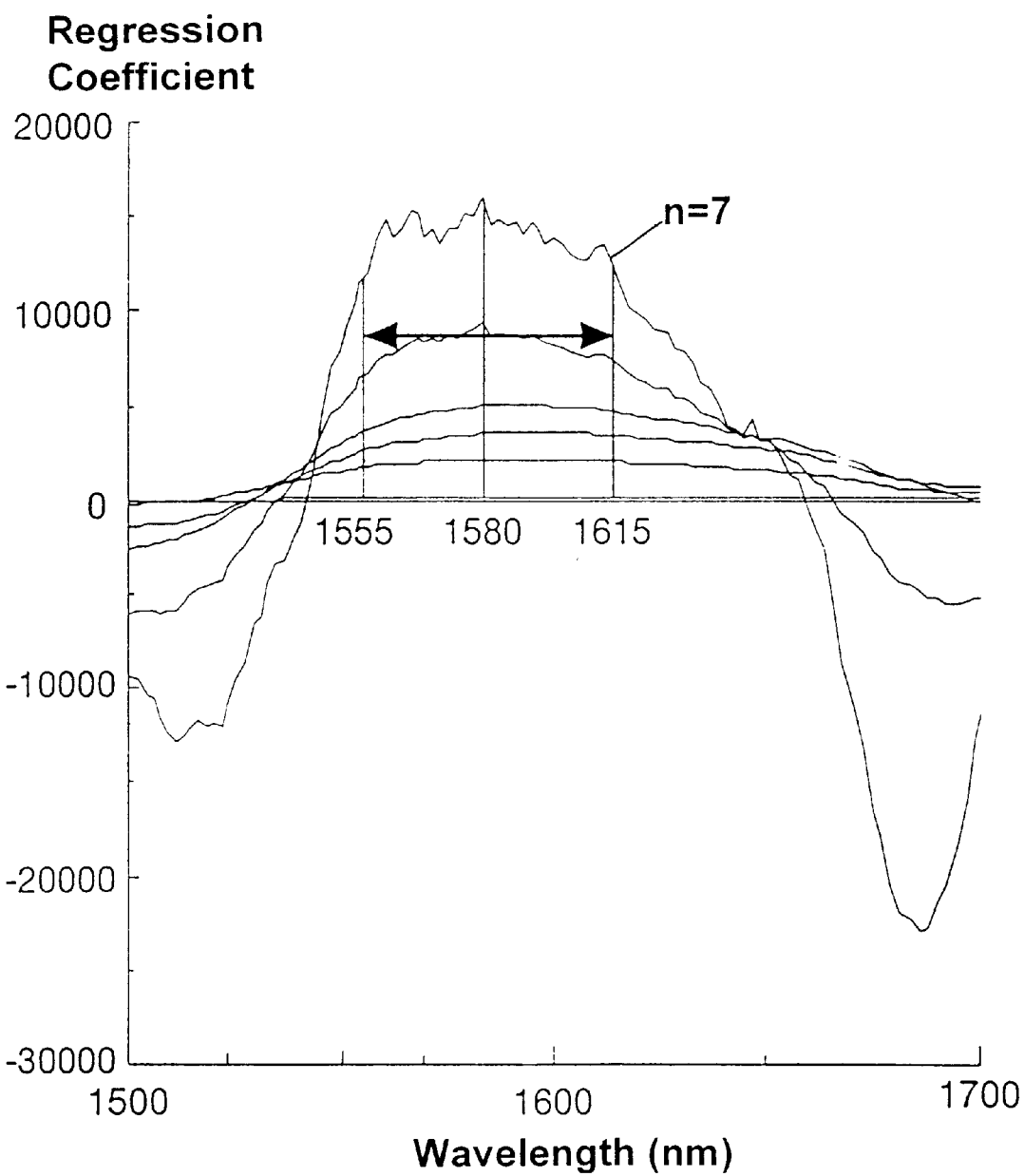
FIG. 11 is a partially-enlarged profile of FIG. 3.
Figure 12:
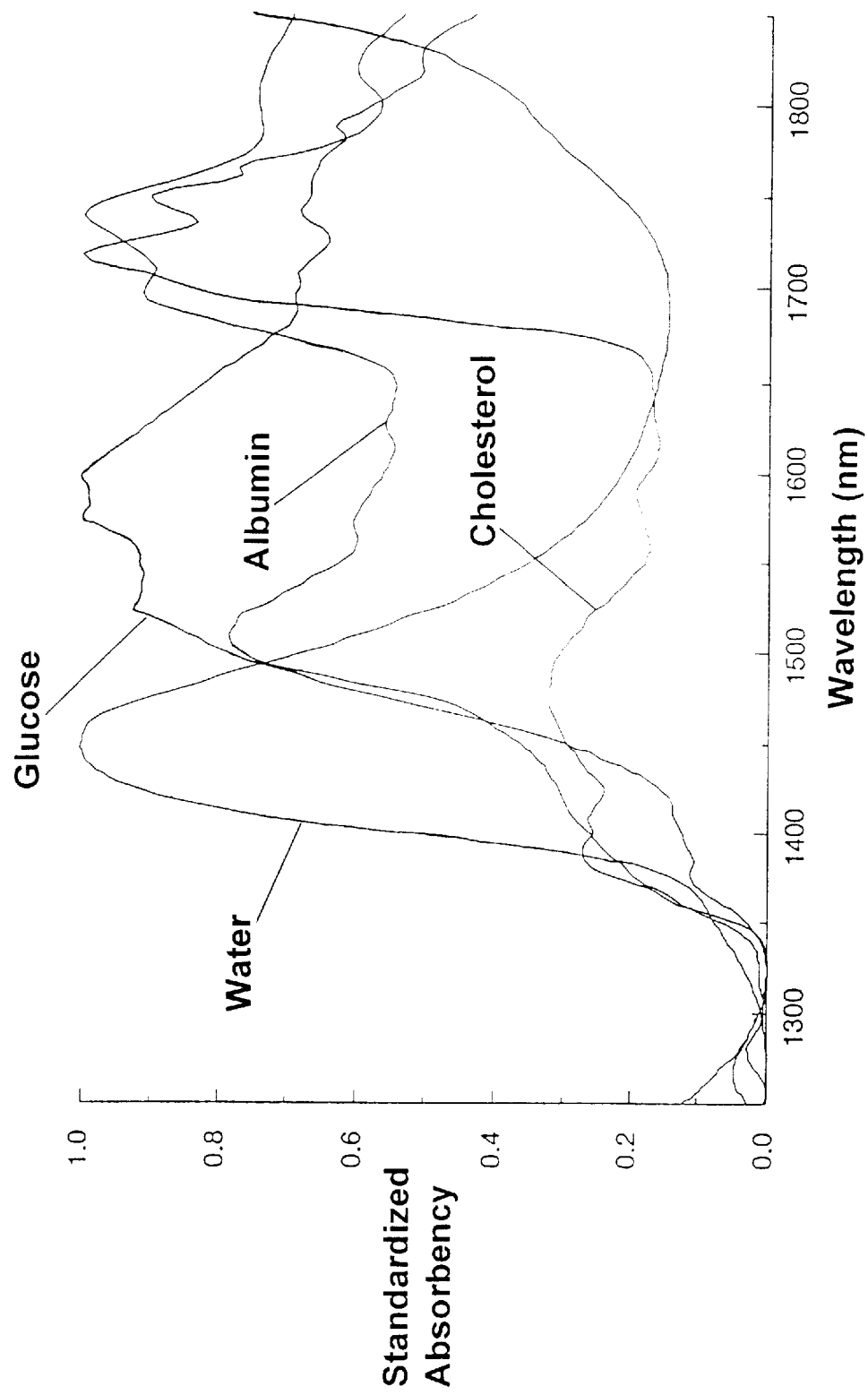
FIG. 12 is absorption spectrums of glucose, albumin, cholesterol, and water, detected over a first harmonic tone region.
Figure 13:
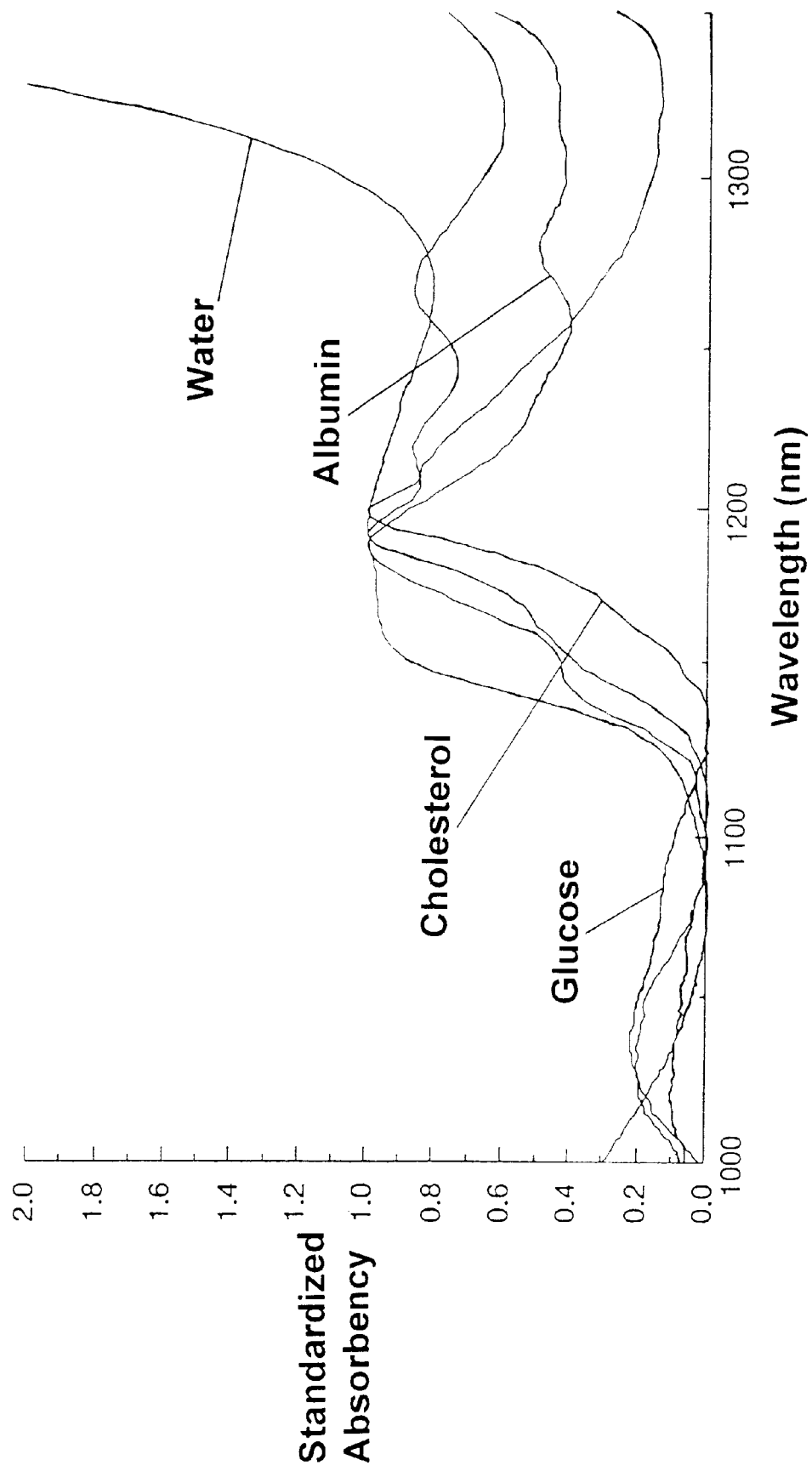
FIG. 13 is absorption spectrums of glucose, albumin, cholesterol, and water, detected over a second harmonic tone region.

The center wavelength of the half-width of the first near-infrared radiation are determined according to the profiles of FIG. 11 which is a partially enlarged view of FIG. 3 obtained in the fourth embodiment. That is, the center wavelength of 1580 nm is a wavelength substantially corresponding to a maximum value of the regression coefficient which is observed within a first wavelength region of 1550 nm to 1650 nm having an absorption peak derived from OH group of glucose molecule. The half-width of 60 nm substantially corresponds to a wavelength region having 70% or more of the maximum value of the regression coefficient within the first wavelength region. When the center wavelength and the half-width are determined by the procedure explained above, there is an advantage of simplifying the operation for determining the glucose concentration without degrading a prediction accuracy of the glucose concentration.

In place of the above-explained procedure, it is possible to determine the center wave length and the half-width of the first near-infrared radiation according to a profile indicative of a relation between wavelength and regression coefficient which is obtained by applying a glucose tolerance test to a subject, measuring absorption spectrums during the glucose tolerance test, and performing a multivariate analysis of the absorption spectrums. The center wavelength and the half-width are not limited to the values used in this embodiment. It is preferred to use the first near-infrared radiation having a center wavelength within a range of 1560 nm to 1640 nm and a half-width of 60 nm or less.

After absorption signals detected by the photo diode 5A is converted to absorbencies, the glucose concentration is determined by the use of a calibration line previously stored in the operating unit. It is preferred to determine the calibration line according to the method of any one of the aforementioned embodiments.

Prior to the multivariate analysis, it is preferred to perform a pretreatment of subtracting a value of wavelength within a near-infrared region from absorption signals or absorbencies. Alternatively, it is preferred to perform a pretreatment of dividing the absorption signals or the absorbencies by the wavelength value. In this embodiment, it is preferred to use as the wavelength value a wavelength selected from a range of 1540±10 nm or 1650±10 nm. In case of using a range of 900 nm to 1350 nm, in which harmonics of a second harmonic tone are observed, it is preferred to use as the wavelength value a wavelength selected from a range of 1060±10 nm or 1130±10nm.

This application is based upon and claims the priority of Japanese patent Application No. 9-72150 filed in Japan on Mar. 25, 1997, the entire contents of which are expressly incorporated by reference herein.

What is claimed is:

1. A method of determining a glucose concentration in a target by using near-infrared spectroscopy, said method comprising the steps of:

projecting near-infrared radiation on said target;

receiving resulting radiation emitted from said target;

performing spectrum analysis of the resulting radiation to detect at least one first absorption signal from a first wavelength region having an absorption peak of OH group derived from glucose molecule, at least one second absorption signal from a second wavelength region having an absorption peak of NH group in said target, and at least one third absorption signal from a third wavelength region having an absorption peak of CH group in said target; and determining said glucose concentration by multivariate analysis of results of said spectrum analysis, in which said first, second and third absorption signals are used as explanatory variables, and said glucose concentration is a criterion variable, wherein said first absorption signal is an absorbency at a first wavelength in said first wavelength region, said second absorption signal is an absorbency at a second wavelength in said second wavelength region, and said third absorption signal is an absorbency at a third wavelength in said third wavelength region, and wherein said first, second and third wavelengths are determined by a method comprising the steps of:

measuring a plurality of absorption spectrums in at least one sample;

performing multivariate analysis of said absorption spectrums to obtain a profile indicative of a relation between wavelength and regression coefficient; and selecting as said first wavelength a wavelength substantially corresponding to a peak of said regression coefficient within said first wavelength region, selecting as said second wavelength a wavelength substantially corresponding to a peak of said regression coefficient within said second wavelength region, and selecting as said third wavelength a wavelength substantially corresponding to a peak of said regression coefficient within said third wavelength region.

2. The method as set forth in claim 1, wherein said first wavelength region is in a range of 1550 nm to 1650 nm, said second wavelength region is in a range of 1480 nm to 1550 nm, and said third wavelength region is in a range of 1650 nm to 1880 nm.

3. The method as set forth in claim 1, wherein said first wavelength region is in a range of 1050 nm to 1130 nm, said second wavelength region is in a range of 1000 nm to 1050 nm, and said third wavelength region is in a range of 1130 nm to 1300 nm.

4. The method as set forth in claim 1, wherein said first wavelength region is in a range of 1600±40 nm, said second wavelength region is in a range of 1530±20 nm, and said third wavelength region is in a range selected from the group consisting of 1685±20 nm, 1715±20 nm, and 1740±20 nm.

5. The method as set forth in claim 1, wherein said plurality of absorption spectrums are measured by a method comprising the steps of:

preparing a plurality of test samples having different concentrations in a system including albumin, glucose, and water; and measuring absorption spectrums of said test samples.

6. The method as set forth in claim 5, wherein fourth and fifth absorption signals are used as said explanatory variables in addition to said first, second and third absorption signals, said fourth and fifth absorption signals are absorbencies at fourth and fifth wavelengths, respectively, and wherein said fourth and fifth wavelengths are determined by the steps of:

performing said multivariate analysis of said absorption spectrums with respect to different principal components to obtain a plurality of profiles indicative of relations between wavelength and regression coefficient;

selecting as said fourth wavelength a wavelength substantially corresponding to an intersection of said profiles at the vicinity of a boundary between said first and second wavelength regions, and selecting as said fifth wavelength a wavelength substantially corresponding to an intersection of said profiles at the vicinity of a boundary between said second and third wavelength regions.

7. The method as set forth in claim 1, wherein said plurality of absorption spectrums are measured by a method comprising the steps of:

applying a glucose tolerance test to a subject; and measuring absorption spectrums of said subject during said glucose tolerance test.

8. The method as set forth in claim 1, wherein said near-infrared radiation projected on said target essentially consists of a first near-infrared radiation having a center wavelength and a half-width within said first wavelength region, a second near-infrared radiation having a center wavelength and a half-width within said second wavelength region, and a third near-infrared radiation having a center wavelength and a half-width within said third wavelength region.

9. The method as set forth in claim 8, wherein said center wavelength and said half-width of said first near-infrared radiation are determined by the steps of:

preparing a plurality of test samples having different concentrations in a system including albumin, glucose, and water;

measuring absorption spectrums of said test samples;

performing a multivariate analysis of said absorption spectrums to obtain a profile indicative of a relation between wavelength and regression coefficient;

selecting as said center wavelength a wavelength substantially corresponding to a maximum value of said regression coefficient within said first wavelength region, and selecting as said half-width a wavelength region substantially corresponding to 70% or more of said maximum value within said first wavelength region.

10. The method as set forth in claim 9, wherein said first near-infrared radiation has said center wavelength within a range of 1560 nm to 1640 nm, and said half-width of 60 nm or less.

11. The method as set forth in claim 8, wherein said center wavelength and said half-width of said first near-infrared radiation are determined by the steps of:

applying a glucose tolerance test to a subject;

measuring absorption spectrums of said subject during said glucose tolerance test;

performing a multivariate analysis of said absorption spectrums to obtain a profile indicative of a relation between wavelength and regression coefficient;

selecting as said center wavelength a wavelength substantially corresponding to a maximum value of said regression coefficient within said first wavelength region, and selecting as said half-width a wavelength region substantially corresponding to 70% or more of said maximum value within said first wavelength region.

12. A method of determining a glucose concentration in a target by using near-infrared spectroscopy, said method comprising the steps of:

projecting near-infrared radiation on said target;

receiving resulting radiation emitted from said target;

performing spectrum analysis of the resulting radiation to detect at least one first absorption signal from a first wavelength region having an absorption peak of OH group derived from glucose molecule, at least one second absorption signal from a second wavelength region having an absorption peak of NH group in said target, and at least one third absorption signal from a third wavelength region having an absorption peak of CH group in said target; and determining said glucose concentration by multivariate analysis of results of said spectrum analysis, in which said first, second and third absorption signals are used as explanatory variables, and said glucose concentration is a criterion variable, wherein said first wavelength region is in a range of 1600±40 nm, said second wavelength region is in a range of 1530±20 nm, and said third wavelength region is in a range selected from the group consisting of 1685±20 nm, 1715±20 nm, and 1740±20 nm.

* * * * *